United States Patent [19]

Wyburn-Mason

[11] 4,402,965

[45] Sep. 6, 1983

[54] TREATMENT OF RHEUMATOID ARTHRITIS AND RELATED DISEASES

[75] Inventor: Roger Wyburn-Mason, Richmond, England

[73] Assignee: John R. A. Simoons, Durham, N.C.

[21] Appl. No.: 405,438

[22] Filed: Aug. 5, 1982

[51] Int. Cl.³ ............................................. A61K 31/42
[52] U.S. Cl. ..................................................... 424/272
[58] Field of Search ......................................... 424/272

Primary Examiner—Stanley J. Friedman
Attorney, Agent, or Firm—Richard T. Laughlin

[57] ABSTRACT

It is believed that rheumatoid arthritis and related collagen and auto-immune diseases are an infection and that various species of free-living (limax) amoebae are the aetiological agent of these diseases. It has been discovered that furazolidone is effective for the treatment of rheumatoid arthritis and other collagen and auto-immune (rheumatoid) diseases.

4 Claims, No Drawings

TREATMENT OF RHEUMATOID ARTHRITIS AND RELATED DISEASES

BACKGROUND OF THE INVENTION

Men and other animals are continually exposed to infection and re-infection by various species and strains of free-living limax amoebae which can be detected in the faeces, nasopharnyx and bronchi. In all parts of the world they form part of the environment. Experimentally in animals they induce changes like those of collagen and autoimmune diseases and are characterized by vasculities, myosotis hepatitis, pyelitis and splenomegaly. They can often be seen in the tissues of animals. Such animals shown lymphadenopathy with an appearance like that of human Hodgkin's disease or a state like that of advance malignant disease. These organisms may also be recovered from all the tissues of cases of collagen and auto-immune diseases and from human and many animal tumors and may also occur in the tissues of apparently healthy individuals. They cannot be identified in ordinary histological sections, but can be demonstrated by immunofluoresence methods.

The definite cause of rheumatoid arthritis is presently unknown. Rheumatoid arthritis is a crippling disease involving any tissue including inflammation of several joints of the body, with swelling, pain and stiffness. Rheumatoid arthritis is a disorder that afflicts about fifteen million people in the United States alone. Successful early treatment may avert the destructive, deforming phase of the disease. Therapy has been directed largely at non-specific suppression of inflammatory and immunologic processes. Aspirin is the cornerstone of therapy for rheumatoid arthritis and can reduce synovial inflammation, improve function and reduce pain in a majority of patients in view of its analgesic action. Widespread interest in rheumatoid arthritis arose when Hench (1949) introduced the use of cortisone in treatment. Chemical compounds which have been commonly used in treating rheumatoid arthritis are corticosteroids, gold salts, antimalarial drugs, immunosuppressive agents and a whole range of so-called non-steroidal drugs, e.g. indomethacin, phenylacetic acid (Ibuprofen), propionic acid (Naproxen) and D-Penicillamine. Most of these drugs bring temporary relief to the arthritic patient but present the danger of side effects and the physician has to balance the potential benefit against the risks. However, arthritis reoccurs following withdrawal of such chemical treatment. For many years rheumatoid arthritis was considered to be an infection (Hollander et al., 1960; Robinson, 1967), but with the advent of the concept of auto-immunity this idea lost favor. Such a view has recently been revived (Lancet, 1970, 2, 303) and is supported by many observations. It is highly likely that the limax amoebae, found in all the collagen and auto-immune diseases, may well be the aetiological agent of these conditions and that antiprotozoal drugs may help by their action on these organisms. The term rheumatoid arthitis and related diseases is to be understood to include diseases such as lupus erythematosis, scleroderma, psoriasis, dermatomyositis, polymyositis, periartheritis nodosa, chronic ulcerative colitis, Still's disease.

The use of a bis-phenyl(2-halophenyl)-1-imidazolylmethane or clotrimazole for treatment of Rheumatoid Arthritis is disclosed in my U.S. patent application Ser. No. 700,914 filed June 29, 1976 now U.S. Pat. No. 4,073,922, issued Feb. 14, 1978, and the use of tinidazole is disclosed in my U.S. Pat. No. 4,119,723. It has also been suggested to use a nitroimidazole in the treatment of rheumatoid arthritis in the Journal of Tropical Medicine and Hygiene (Vol. 75) pags. 64 to 66 March 1972. It is believed that the nitro group in the imidazole ring is related to metronidiazole which is not effective in the treatment of rheumatoid arthritis in small doses.

Various anti-protozoal drugs were tried on the cases of rheumatoid disease or of various localized manifestations of this. The substances investigated were 4-aminoquinolines (chloroquine), hydroxychloroquine (plaquenil), amodiaquine (camoquin); copper sulphate; bile salts (dehydrocholine), which are effective in killing the trophozooites of many amoebae in the concentration found in the small intestine; and clotrimazole (canesten). All of these were actually shown experimentally to kill limax amoebae. In addition, other antiprotozoal drugs were also investigated. They included suramin, pentamidine, dehydro-emetine (DHE or mebadin), metronidiazole (flagyl), nimorazole (naxogin Erba)), phanquone (entobex) and diloxanide (furamide).

The various substances tested above were tried on cases of rheumatoid arthritis of varying severity, systemic lupus erythematosus, dermatomyositis and other manifestations of collagen and auto-immune disease and observations made on the clinical condition, oedema, morning stiffness, E.S.R., plasma proteins, RF, ANF and organ-specific antibodies in the serum. No attempt at a double-blind trial was made as it became obvious, fairly early or even the day after commencing treatment, whether beneficial effect was obtained and furthermore, symptomatic improvement is associated with improvement or disappearance of the abnormal blood changes, indicating that the drug was effective and improvement not due to suggestion. No beneficial effect was obtained from flagyl, naxogin, entobex, suramin or furamide in the doses used. However, Abd-Rabbo et al. (1972), using a derivative of nitro-imidazole (naxogin), BT 985 Merck A.G., which is active against amoebae, giardia and trichomonas, obtained beneficial effects in one case of systemic lupus erythematosus and nine of ten cases of rheumatoid disease. The drug was given in doses of 250 mg. daily for 14–39 days. In the follow-up period of 3–6 months no treatment was given and it was noted that the pain recurred, yet not to the same degree as before medication.

The method of determining the anti-protozoal activity of drugs on limax amoebae was described by Fulton, C. Methods in Cell Biology (edited by D. M. Prescott), p. 341, New York, 1970 and followed by Jamieson and Anderson in Lancet, 1974, 1, 261. All experiments were performed using 5-day-old 5 ml. cultures of amoebae in the axenic medium "A" of Fulton. A standard inoculum of 100 c.mm. of differing concentrations of amoebae was added to each 1 ml. tube containing the dilutions of the compound to be tested (dissolved initially in dimethyl sulfoxide) or other drugs in the axenic medium. The tubes were incubated for 5 days and 37 C. and the final concentration per c.mm. was compared with the initial count to determine percentage kill.

It has now been found that rheumatoid arthritis can be effectively treated with a compound having antiprotozoal activity of the formula:

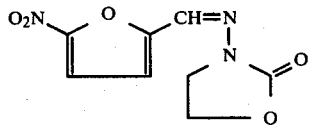

This compound in furazolidone is [3-(5-nitrofurfurylidene amino)-2-oxazolidinone]. The compound is known to have anti-protozoal activity suitable for topical application. The compound is soluble in water and can be prepared by the procedures disclosed in U.S. Pat. Nos. 2,759,931 and 2,927,110.

The diagnosis of active rheumatoid arthritis in six cases, was consistent with the criteria of the American Rheumatism Association. The patients were not hospitalized or confined to bed. They continued to take the drugs they were being treated with when first seen. Serial investigations were carried out before and repeatedly during and after treatment. Furazolidone was administered orally in a dosage of 100 mgms. four times a day for seven days (approximately 6 mg. per kilogram of body weight per day), suitable doses range from about 4 to 12 mg. per kilogram of body weight. With this dosage of the drug beginning 24–36 hours after taking it there almost invariably occurs an exacerbation of the active inflammatory changes in the affected joints with increased heat, pain and swelling and other parts of the body not previously affected may also be involved with generalized malaise and often sweating. This may last for one to two weeks and then disappear with general improvement in the patient's symptoms. With successive doses this reaction becomes less and finally disappears and as the course of treatment progresses the signs of active rheumatoid disease also disappears. This response constitutes an Herxheimer reaction and its occurrence with furazolidone anti-protozoal drug, indicates with certainty the presence in the affected tissues of an organism which is acted on by the drug. Steroid and other treatments may then be tapered off. Furazolidone was administered to patients ranging from 43–62 years. Symptoms had been present for two to fifteen years. Patients have been followed for 6–9 months without evidence of recurrence of activity of the disease and with return of the sedimentation rate to normal. The drug thus eventually completely reversed all the manifestations of activity in rheumatoid disease when other drugs had failed. In larger doses it may cause an Herxheimer response indicating the existence in the lesions of rheumatoid disease of an organism, presumably a protozoan, affected by the drug. It caused no other side effects except occasional pruritus when alcohol was taken.

The therapeutically effective compound can be used either as such or in combination with pharmaceutically acceptable carriers. Suitable forms of administration in combination with various inert carriers are tablets, capsules, powders, aqueous syspensions, syrups and the like. In the aforesaid case, the therapeutically active compound should be present in the total mixture at a concentration of about 0.5 to 90 percent by weight, i.e., in quantities which suffice to attain the range of dosage mentioned above. Tablets may also contain fillers such as starch, avicel, lactose, calcium carbonate or dicalcium phosphate together with various additives such as dyes and binders such as polyvinylpyrrolidine, methylcellulose, gelatin and the like. It is further required to add lubricants such as magnesium stearate, sodium laurylsulphate and talc for producing tablets. Tablets may be filmcoated.

EXAMPLE I

|  | Weight |
| --- | --- |
| Micronized furazolidone | 1.0 Kg. |
| Cornstarch powder | 0.3 Kg. |
| Avicel (microcrystalline cellulose)PH 102 | 1.54 Kg. |
| Methocel 50 HG, 60 CPS | 80.0 gm. |
| Purified water | q.s. |

The furazolidone powder is mixed in a suitable blender with the other components and the granulated mass is passed through an oscillator equipped with a 20-mesh screen. The granules are dried in a vacuum oven at 40° C. until a moisture content of less than 3% is reached. The granules are screened through a 20-mesh screen, lubricated with stearic acid 30 gm. and magnesium stearate 50 gm. The final mix is compressed into tablets of 300 mg. each, which contain 100 mg. of furazolidone per tablet and can be used for oral administration.

Any departure from the foregoing description which conforms to the present invention is intended to be included within the scope of the claims.

What is claimed is:

1. A method for producing remission in patients suffering from active rheumatoid arthritis which comprises administering orally to such a patient an affective amount of furazolidone.

2. The method of combatting rheumatoid arthritis of claim 1 which comprises orally administering to the infected subject furazolidone in a daily amount of about 4 to about 12 miligrams per kilogram of body weight.

3. The method of claim 2 wherein said daily amount is 100 mgms administered four times per day.

4. The method of claim 2 wherein said daily amount is 100 mg administered four times per day for seven days and repeated every six months.

* * * * *